United States Patent [19]
Alexander et al.

[11] 3,939,177
[45] Feb. 17, 1976

[54] 4-AMINOMETHYL-9-BENZYL-1,2,3,4-TETRAHYDROCARBAZOLES

[75] Inventors: Ernest John Alexander, East Greenbush; Aram Mooradian, Schodack, both of N.Y.

[73] Assignee: Sterling Drug Inc., New York, N.Y.

[22] Filed: Nov. 22, 1972

[21] Appl. No.: 308,674

[52] U.S. Cl. ...... 260/315; 260/268 TR; 260/293.61; 424/250; 424/267; 424/274
[51] Int. Cl.² .................................... C07D 209/86
[58] Field of Search .................................. 260/315

[56] References Cited
UNITED STATES PATENTS
3,752,823   8/1973   McManus ........................ 260/315

OTHER PUBLICATIONS
JACS 79: 3561–3564, (1957), Shaw et al.

Primary Examiner—Sherman D. Winters
Attorney, Agent, or Firm—Frederik W. Stonner; B. Woodrow Wyatt

[57] ABSTRACT

Novel 4-$R_1R_2NCH_2$-9-benzyl-6-$R_3$-7-$R_4$-1,2,3,4-tetrahydrocarbazoles having antibacterial activity are disclosed. The compounds are prepared by the chemical reduction of the corresponding 4-$R_1R_2NCO$-9-benzyl-6-$R_3$-7-$R_4$-1,2,3,4-tetrahydrocarbazoles.

8 Claims, No Drawings

4-AMINOMETHYL-9-BENZYL-1,2,3,4-TETRAHYDROCARBAZOLES

This invention relates to compositions of matter classified in the art of chemistry as 1,2,3,4-tetrahydrocarbazoles.

In one aspect the invention sought to be patented resides in the chemical compounds designated as 4-$R_1R_2NCH_2$-9-benzyl-6-$R_3$-7-$R_4$-1,2,3,4-tetrahydrocarbazoles having the formula:

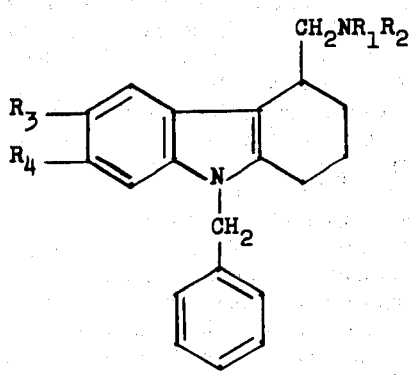

I wherein
$R_1$ and $R_2$ are each hydrogen, lower-alkyl, or benzyl, or
$NR_1R_2$ is 1-pyrrolidyl, 1-piperidyl, or 4-phenyl-1-piperazinyl; and
$R_3$ and $R_4$ are each hydrogen, lower-alkyl, or lower-alkoxy.

In a second aspect the invention sought to be patented resides in the novel chemical compounds designated as 4-$R_1R_2NCO$-9-benzyl-6-$R_3$-7-$R_4$-1,2,3,4-tetrahydrocarbazoles having the formula:

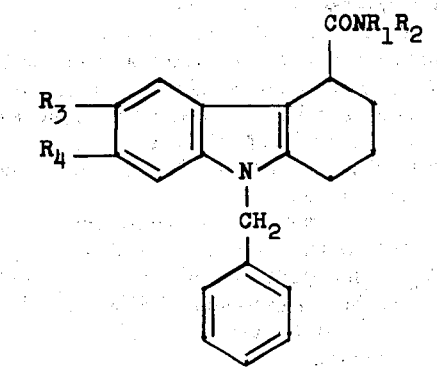

II wherein
$R_1$ and $R_2$ are each hydrogen, lower-alkyl, or benzyl, or
$NR_1R_2$ is 1-pyrrolidyl, 1-piperidyl, or 4-phenyl-1-piperazinyl; and
$R_3$ and $R_4$ are each hydrogen, lower-alkyl, or lower-alkoxy.

The compounds of the invention having formula I exhibit antibacterial activity as more fully described hereinbelow.

The compounds of the invention having formula II are useful as intermediates in the preparation of compounds of this invention having formula I.

The compounds having formula I are prepared by chemical reduction of the corresponding 4-$R_1R_2NCO$-9-benzyl-6-$R_3$-7-$R_4$-1,2,3,4-tetrahydrocarbazoles (II). The reduction is carried out by treating the amide II with a suitable chemical reducing agent in a suitable solvent, e.g., lithium aluminum hydride in ether, tetrahydrofuran, di-n-butyl ether, or dioxane; or diborane in tetrahydrofuran or diglyme. The reduction is carried out preferably at a temperature of about 20°C. to 100°C. for about 1 to 24 hours. The reaction is conveniently carried out by treating the amide II in tetrahydrofuran under reflux with a slight molar excess of lithium aluminum hydride for about 4 to about 6 hours.

Alternatively, the compounds of formula I where $R_1$ and $R_2$ are hydrogen are prepared by chemical reduction of the corresponding 4-cyano-9-benzyl-6-$R_3$-7-$R_4$-1,2,3,4-tetrahydrocarbazoles (III) using the procedures described hereinbefore for the reduction of the amide II.

The intermediate 4-$R_1R_2NCO$-9-benzyl-6-$R_3$-7-$R_4$-1,2,3,4-tetrahydrocarbazole (II) is prepared from the corresponding 9-benzyl-6-$R_3$-7-$R_4$-1,2,3,4-tetrahydrocarbazole-4-carboxylic acid halide (IV), where halide is chloride or bromide, by reaction with an amine of the formula $R_1R_2NH$ (V). The reaction is carried out by treating the acid halide in a suitable solvent, e.g., benzene, methylene dichloride or pyridine, with at least one equivalent of amine V, at temperatures from about 0°C. to ambient temperatures. Preferably, the reaction is carried out in the presence of at least one equivalent of a suitable acid-acceptor, e.g., triethylamine, pyridine or potassium bicarbonate; if desired, excess amine V may be used as the acid-acceptor. The reaction is conveniently carried out by reacting the acid halide IV with at least two equivalents of amine V, in aqueous solution if desired, in benzene with ice-bath cooling.

The intermediate cyano compound III is prepared by dehydration of the corresponding 4-carbamyl-9-benzyl-6-$R_3$-7-$R_4$-1,2,3,4-tetrahydrocarbazole (II, $R_1 = R_2 = H$). The reaction is carried out in a suitable solvent, e.g., benzene or pyridine, in the presence of a suitable dehydrating agent, e.g., phosphorus oxychloride, thionyl chloride, or benzenesulphonyl chloride, preferably at temperatures of about 20°C. to 100°C. The reaction can be conveniently carried out by treating the 4-carbamyl compound in pyridine with benzenesulphonyl chloride on a steam bath for about one to two hours.

The intermediate acid halide IV is prepared from the corresponding 9-benzyl-6-$R_3$-7-$R_4$-1,2,3,4-tetrahydrocarbazole-4-carboxylic acid (VI) using standard procedures, e.g., by reaction in a suitable solvent, e.g., ethylene dichloride, chloroform, or benzene, with an appropriate halogenating agent, such as thionyl chloride or oxalyl chloride. The reaction is conveniently carried out by reacting an alkali metal salt, e.g., sodium salt, of the carboxylic acid VI in benzene with a slight excess of thionyl chloride.

The 9-benzyl-6-$R_3$-7-$R_4$-1,2,3,4-tetrahydrocarbazole-4-carboxylic acid (VI) and intermediates therefor belong to classes of compounds which together with detailed methods for the preparation thereof are disclosed in U.S. Pat. No. 3,687,969. Thus, they are prepared for example by reaction of N-(4-$R_3$-3-$R_4$-phenyl)-N-benzylamine (VII) with 6-bromocyclohexanone-2-carboxylic acid ester (VIII), e.g., methyl or ethyl ester, and subsequent hydrolysis; the intermediate N-phenyl-N-benzylamines (VII) are known compounds that are readily prepared by standard procedures, e.g., from the corresponding known anilines and benzaldehydes.

As used throughout this specification, the terms lower-alkyl and lower-alkoxy mean such groups containing from one to six carbon atoms which can be arranged as straight or branched chains, and, without limiting the generality of the foregoing, are illustrated by methyl, ethyl, propyl, isopropyl, butyl, sec-butyl, tert-butyl, amyl, hexyl, and the like for lower-alkyl; and methoxy, ethoxy, propoxy, isobutoxy, tert-butoxy, hexyloxy, and the like for lower-alkoxy.

The compounds of the invention having formula I are useful both in the free base form and in the form of acid-addition salts, and both forms are within the purview of the invention. The acid-addition salts are simply a more convenient form for use, and in practice, use of the salt form inherently amounts to use of the base form. When the compounds of the invention having formula I are to be utilized for pharmaceutical purposes, the acids which can be used to prepare the acid-addition salts include preferably those which produce, when combined with the free base, medicinally acceptable salts, that is, salts whose anions are relatively innocuous to the animal organism in medicinal doses of the salts, so that the beneficial properties inherent in the free base are not vitiated by side effects ascribable to the anions. Appropriate medicinally acceptable salts within the scope of the invention are those derived from mineral acids such as hydrochloric acid, hydrobromic acid, hydriodic acid, nitric acid, phosphoric acid, sulfamic acid, and sulfuric acid; and organic acids such as acetic acid, citric acid, tartaric acid, lactic acid, cyclohexanesulfamic acid, methanesulfonic acid, ethanesulfonic acid, benzenesulfonic acid, p-toluenesulfonic acid, quinic acid, and the like, giving the hydrochloride, hydrobromide, hydriodide, nitrate, phosphate, sulfamate, acetate, citrate, tartrate, lactate, cyclohexanesulfamate, methanesulfonate, ethanesulfonate, benzenesulfonate, p-toluenesulfonate and quinate respectively.

The acid-addition salts of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution or dilution of the solution with a solvent in which the salt is insoluble or only slightly soluble.

Although medicinally acceptable salts of said basic compounds are preferred for pharmaceutical purposes, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a medicinally acceptable salt by ion exchange procedures.

The compounds of formula I possess useful antibacterial activity, thus indicating the utility of the compounds of formula I as antibacterial agents.

The antibacterial activities were determined using a modification of the Autotiter method described by Goss et al., Applied Microbiology 16 (No. 9), 1414–1416 (1968) in which a 1,000 mcg./ml. solution of the test compound is prepared. To the first cup of the Autotray is added 0.1 ml. of the test solution. Activation of the Autotiter initiates a sequence of operations by which 0.05 ml. of the test compound solution is withdrawn from this cup by a Microtiter transfer loop and diluted in 0.05 ml. of sterile semi-synthetic medium (glucose). After this operation, 0.05 ml. of inoculated semi-synthetic medium is added automatically to each cup. The overall operation results in final drug concentrations ranging from 500 to 0.06 mcg./ml. in twofold decrements. The Autotray is incubated for 18–20 hours at 37°C., at which time the trays are examined visually for growth as evidenced by turbidity, and the concentration of the last sample in the series showing no growth (or no turbidity) is recorded as the minimal inhibitory concentration (MIC).

By way of illustration, the compounds of Examples 1B to 8B inclusive and 9C were found to be antibacterially effective against *Staphylococcus aureus* at concentrations from 7.8 mcg./ml. to 500 mcg./ml.; and the compound of Example 10C was found to be antibacterially effective against *Pseudomonas aeruginosa* at a concentration of 125 mcg./ml.; additionally, certain of these compounds were found also to be antibacterially effective, as disclosed specifically in the examples hereinbelow, against one or more of the following microorganisms: *Pseudomonas aeruginosa*, *Escherichia coli*, and *Proteus vulgaris*.

The actual determination of the numerical biological data definitive for a particular compound is readily determined by standard test procedures by technicians having ordinary skill in pharmacological test procedures, without the need for any extensive experimentation.

The compounds of the invention having formula I can be formulated for use by preparing a dilute solution in an aqueous medium or in a solution containing a surfactant, or alternatively in an organic medium in which the compounds are soluble, for example ethyl alcohol, and are applied to a surface to be disinfected by conventional means such as spraying, swabbing, immersion, and the like. Alternatively, the compounds can be formulated as ointments or creams by incorporating them in conventional ointment or cream bases, for example alkylpolyether alcohols, cetyl alcohol, stearyl alcohol, and the like, or as jellies by incorporating them in conventional jelly bases as glycerol and tragacanth. They can also be formulated for use as aerosol sprays or foams.

The molecular structures of the compounds of the invention were assigned on the basis of the method of their synthesis and study of their infrared spectra, and confirmed by the correspondence between calculated and found values for the elementary analysis for representative examples.

The invention is illustrated by the following examples without, however, being limited thereto.

EXAMPLE 1

A. To 0.88 g. of sodium hydride in 200 ml. dry benzene was added portionwise 12.3 g. of 9-benzyl-6-methoxy-1,2,3,4-tetrahydrocarbazole-4-carboxylic acid and the mixture was stirred for one hour. To this mixture was added dropwise 2.7 ml. of thionyl chloride, stirring was continued for one-half hour and the mixture containing the resulting 9-benzyl-6-methoxy-1,2,3,4-tetrahydrocarbazole-4-carboxylic acid chloride was poured into 32 ml. of 25% aqueous dimethylamine with ice-bath cooling. The mixture was stirred for 1 hour, washed with water, sodium bicarbonate and saturated salt solution, dried, diluted with n-pentane, cooled and filtered to give 7.9 g. of 4-dimethylaminocarbonyl-9-benzyl-6-methoxy-1,2,3,4-tetrahydrocarbazole, m.p. 153°–155°C.

B. To 1.2 g. of lithium aluminum hydride in 200 ml. of dry tetrahydrofuran was added portionwise 11.4 g. of 4-dimethylaminocarbonyl-9-benzyl-6-methoxy-1,2,3,4-tetrahydrocarbazole and the mixture was heated under reflux for 5 hours and allowed to stand at room temperature for 15 hours. Water (2.4 ml.) was added to the mixture which was then heated under reflux for 1 hour, filtered hot, and the filtrate was treated with darco, filtered and evaporated under reduced pressure to give 12 g. of crude residue consisting largely of 4-dimethylaminomethyl-9-benzyl-6-methoxy-1,2,3,4-tetrahydrocarbazole, 4 g. of which was dissolved in ether and treated with ethereal hydrogen chloride. The resulting solid was filtered to give 2.6 g. of 4-dimethylaminomethyl-9-benzyl-6-methoxy-1,2,3,4-tetrahydrocarbazole hydrochloride, m.p. 238°–240°C. (absolute alcohol/ether).

4-Dimethylaminomethyl-9-benzyl-6-methoxy-1,2,3,4-tetrahydrocarbazole hydrochloride was found to be antibacterially effective against *Staphylococcus aureus* at 62.5 mcg./ml.

EXAMPLE 2

A. Following a procedure similar to that described in Example 1A but using 2.13 g. of sodium hydride in 510 ml. of benzene, 2.74 g. of 9-benzyl-1,2,3,4-tetrahydrocarbazole-4-carboxylic acid, 6.6 ml. of thionyl chloride, and 7.8 ml. of 25% aqueous dimethylamine, there was obtained 2.6 g. of 4-dimethylaminocarbonyl-9-benzyl-1,2,3,4-tetrahydrocarbazole, m.p. 180°–183°C. (tetrahydrofuran/n-pentane).

B. Following a procedure similar to that described in Example 1B but using 2.1 g. of lithium aluminum hydride in 200 ml. of tetrahydrofuran, and 17.3 g. of 4-dimethylaminocarbonyl-9-benzyl-1,2,3,4-tetrahydrocarbazole, there was obtained 18.4 g. of crude residue consisting largely of 4-dimethylaminomethyl-9-benzyl-1,2,3,4-tetrahydrocarbazole, 3 g. of which yielded 2.3 g. of 4-dimethylaminomethyl-9-benzyl-1,2,3,4-tetrahydrocarbazole hydrochloride, m.p. 208°–210°C.

4-Dimethylaminomethyl-9-benzyl-1,2,3,4-tetrahydrocarbazole hydrochloride was found to be antibacterially effective against *Staphylococcus aureus* and *Escherichia coli* at 125 mcg./ml.

EXAMPLE 3

A. Following a procedure similar to that described in Example 1A but using 1.97 g. of sodium hydride in 470 ml. of benzene, 25 g. of 9-benzyl-1,2,3,4-tetrahydrocarbazole-4-carboxylic acid, 6.1 ml. of thionyl chloride, and 14 g. of piperidine in a small amount of water, there was obtained 3.5 g. of 4-[(1-piperidyl)carbonyl]-9-benzyl-1,2,3,4-tetrahydrocarbazole, m.p. 140°–143°C. (tetrahydrofuran/n-pentane).

B. Following a procedure similar to that described in Example 1B but using 2.6 g. of lithium aluminum hydride in 250 ml. of tetrahydrofuran, and 23.7 g. of 4-[(1-piperidyl)carbonyl]-9-benzyl-1,2,3,4-tetrahydrocarbazole, there was obtained 22.3 g. of crude residue consisting largely of 4-[(1-piperidyl)methyl]-9-benzyl-1,2,3,4-tetrahydrocarbazole, 10 g. of which yielded 5.4 g. of 4-[(1-piperidyl)methyl]-9-benzyl-1,2,3,4-tetrahydrocarbazole hydrochloride, m.p. 249°–252°C.

4-[(1-Piperidyl)methyl]-9-benzyl-1,2,3,4-tetrahydrocarbazole hydrochloride was found to be antibacterially effective against *Staphylococcus aureus* at 31.2 mcg./ml.

EXAMPLE 4

A. Following a procedure similar to that described in Example 1A but using 2.66 g. of sodium hydride in 240 ml. of benzene, 34 g. of 9-benzyl-1,2,3,4-tetrahydrocarbazole-4-carboxylic acid, 8.3 ml. of thionyl chloride, and 19 g. of pyrrolidine (neat), there was obtained 8 g. of 4-[(1-pyrrolidyl)-carbonyl]-9-benzyl-1,2,3,4-tetrahydrocarbazole, m.p. 161°–163°C. (tetrahydrofuran/n-pentane).

B. Following a procedure similar to that described in Example 1B but using 2.6 g. of lithium aluminum hydride in 250 ml. of tetrahydrofuran, and 23.1 g. of 4-[(1-pyrrolidyl)carbonyl]-9-benzyl-1,2,3,4-tetrahydrocarbazole, there was obtained 20.1 g. of crude residue consisting largely of 4-[(1-pyrrolidyl)methyl]-9-benzyl-1,2,3,4-tetrahydrocarbazole, 8 g. of which yielded 2.6 g. of 4-[(1-pyrrolidyl)methyl]-9-benzyl-1,2,3,4-tetrahydrocarbazole hydrochloride, m.p. 232°–234°C.

4-[(1-Pyrrolidyl)methyl]-9-benzyl-1,2,3,4-tetrahydrocarbazole hydrochloride was found to be antibacterially effective against *Staphylococcus aureus*, *Pseudomonas aeruginosa*, *Escherichia coli* and *Proteus vulgaris* at 62.5 mcg./ml., 500 mcg./ml., 125 mcg./ml. and 500 mcg./ml. respectively.

EXAMPLE 5

A. Following a procedure similar to that described in Example 1A but using 0.72 g. of sodium hydride in 175 ml. of benzene, 10 g. of 9-benzyl-6-methoxy-1,2,3,4-tetrahydrocarbazole-4-carboxylic acid, 2.2 ml. of thionyl chloride, and 1.9 g. of methylamine in a small amount of benzene, there was obtained 7.6 g. of 4-methylaminocarbonyl-9-benzyl-6-methoxy-1,2,3,4-tetrahydrocarbazole, m.p. 163°–166°C. (ether).

B. Following a procedure similar to that described in Example 1B but using 0.9 g. of lithium aluminum hydride in 150 ml. of tetrahydrofuran, and 7.6 g. of 4-methylaminocarbonyl-9-benzyl-6-methoxy-1,2,3,4-tetrahydrocarbazole, there was obtained 8.2 g. of crude residue consisting largely of 4-methylaminomethyl-9-benzyl-6-methoxy-1,2,3,4-tetrahydrocarbazole, which yielded 4.8 g. of 4-methylaminomethyl-9-benzyl-6-methoxy-1,2,3,4-tetrahydrocarbazole hydrochloride, m.p. 259°–261°C.

4-Methylaminomethyl-9-benzyl-6-methoxy-1,2,3,4-tetrahydrocarbazole hydrochloride was found to be antibacterially effective against *Staphylococcus aureus* at 62.5 mcg./ml.

EXAMPLE 6

A. Following a procedure similar to that described in Example 1A but using 1.3 g. of sodium hydride in 310 ml. of benzene, 17.2 g. of 9-benzyl-1,2,3,4-tetrahydrocarbazole-4-carboxylic acid, 4.1 ml. of thionyl chloride, 9.1 g. of N-phenylpiperazine, and 30 ml. of triethylamine (as acid-acceptor), there was obtained 8.6 g. of 4-[(4-phenyl-1-piperazinyl)carbonyl]-9-benzyl-1,2,3,4-tetrahydrocarbazole, m.p. 135°–137°C. (ethyl acetate/n-pentane).

B. Following a procedure similar to that described in Example 1B but using 1.1 g. of lithium aluminum hydride in 75 ml. of tetrahydrofuran, and 12.6 g. of 4-[(4-phenyl-1-piperazinyl)-carbonyl]-9-benzyl-1,2,3,4-tetrahydrocarbazole, there was obtained 12.3 g. of crude residue consisting largely of 4-[(4-phenyl-1-piperazinyl)methyl]-9-benzyl-1,2,3,4tetrahydrocarbazole, which yielded 5 g. of 4-[(4-phenyl-1-piperazinyl)methyl]-9-benzyl-1,2,3,4-tetrahydrocarbazole hydrochloride, m.p. 273°–274°C. (dimethylformamide/ether).

4-[(4-Phenyl-1-piperazinyl)methyl]-9-benzyl-1,2,3,4-tetrahydrocarbazole hydrochloride was found to be antibacterially effective against *Staphylococcus aureus* at 250 mcg./ml.

EXAMPLE 7

A. Following a procedure similar to that described in Example 1A but using 0.24 g. of sodium hydride in 100 ml. of benzene, 5.8 g. of 9-benzyl-6-methoxy-1,2,3,4-tetrahydrocarbazole-4-carboxylic acid, 1.28 ml. of thionyl chloride, 3 g. of N-phenylpiperazine, and 10 ml. of triethylamine (as acid-acceptor) in a small amount of water, there was obtained 3.1 g. of 4-[(4-phenyl-1-piperazinyl)carbonyl]-9-benzyl-6-methoxy-1,2,3,4-tetrahydrocarbazole, m.p. 170°–172°C. (benzene/n-hexane).

B. Following a procedure similar to that described in Example 1B but uisng 0.38 g. of lithium aluminum hydride in 100 ml. of tetrahydrofuran, and 5 g. of 4-[(4-phenyl-1-piperazinyl)carbonyl]-9-benzyl-6-methoxy-1,2,3,4-tetrahydrocarbazole, there was obtained crude residue consisting largely of product in free base form which on recrystallization from tetrahydrofuran/n-hexane/ether yielded 3.5 g. of 4-[(4-phenyl-1-piperazinyl)methyl]-9-benzyl-6-methoxy-1,2,3,4-tetrahydrocarbazole, m.p. 142°–143°C.

4-[(4-Phenyl-1-piperazinyl)methyl]-9-benzyl-6-methoxy-1,2,3,4-tetrahydrocarbazole was found to be antibacterially effective against *Staphylococcus aureus*, *Pseudomonas aeruginosa* and *Escherichia coli* at 500 mcg./ml.

EXAMPLE 8

A. Following a procedure similar to that described in Example 1A but using 0.72 g. of sodium hydride in 170 ml. of benzene, 10 g. of 9-benzyl-6-methoxy-1,2,3,4-tetrahydrocarbazole-4-carboxylic acid, 2.2 g. of thionyl chloride, and 6.4 g. of benzylamine, there was obtained 2.9 g. of 4-benzylaminocarbonyl-9-benzyl-6-methoxy-1,2,3,4-tetrahydrocarbazole, m.p. 176°–179°C. (tetrahydrofuran).

B. A mixture of 24.8 g. of 4-benzylaminocarbonyl-9-benzyl-6-methoxy-1,2,3,4-tetrahydrocarbazole in 460 ml. of tetrahydrofuran was added dropwise to 240 ml. of a one molar solution of diborane in tetrahydrofuran at 0°C. in a nitrogen atmosphere, and the solution was allowed to stand at room temperature for 64 hours. Chilled 6-N-hydrochloric acid (37 ml.) was added, and the solution was concentrated on a steam bath. The resulting solid was filtered and recrystallized from methanol-ether to give 7.3 g. of 4-benzylaminomethyl-9-benzyl-6-methoxy-1,2,3,4-tetrahydrocarbazole hydrochloride, m.p. 274°–278°C.

4-Benzylaminomethyl-9-benzyl-6-methoxy-1,2,3,4-tetrahydrocarbazole hydrochloride was found to be antibacterially effective against *Staphylococcus aureus* at 7.8 mcg./ml.

EXAMPLE 9

A. Following a procedure similar to that described in Example 1A but using 2.4 g. of sodium hydride in 580 ml. of benzene, 33.6 g. of 9-benzyl-6-methoxy-1,2,3,4-tetrahydrocarbazole-4-carboxylic acid, 7.4 ml. of thionyl chloride, and 47 ml. of concentrated ammonium hydroxide, there was obtained 12.5 g. of 4-carbamyl-9-benzyl-6-methoxy-1,2,3,4-tetrahydrocarbazole, m.p. 156°–158°C. (ethyl alcohol/tetrahydrofuran/water).

B. To 47.9 g. of 4-carbamyl-9-benzyl-6-methoxy-1,2,3,4-tetrahydrocarbazole in 140 ml. of pyridine was added 17.9 ml. of benzenesulphonyl chloride, and the mixture was warmed on a steam bath until solution was complete, allowed to stand for 15 hours at room temperature and poured into water. The mixture was chilled, and the resulting precipitate was filtered, washed with dilute hydrochloric acid and water, and dried to give 24.5 g. of 4-cyano-9-benzyl-6-methoxy-1,2,3,4-tetrahydrocarbazole, m.p. 130°–137°C.

C. To 1.3 g. of lithium aluminum hydride in 200 ml. of tetrahydrofuran was added portionwise 10 g. of 4-cyano-9-benzyl-6-methoxy-1,2,3,4-tetrahydrocarbazole, and the mixture was heated under reflux for 5 hours. Water (2.6 ml.) was added and heating under reflux was continued 1 hour and the mixture was then filtered. The filtrate was evaporated to dryness under reduced pressure and an ethyl acetate solution of the resulting crude residue, consisting largely of 4-aminomethyl-9-benzyl-6-methoxy-1,2,3,4-tetrahydrocarbazole, was treated with 1.8 ml. of glacial acetic acid and chilled. The resulting solid was filtered, washed with ethyl acetate and ether, and dried to give 3.7 g. of 4-aminomethyl-9-benzyl-6-methoxy-1,2,3,4-tetrahydrocarbazole acetate, m.p. 171°–175°C.

4-Aminomethyl-9-benzyl-6-methoxy-1,2,3,4-tetrahydrocarbazole acetate was found to be antibacterially effective against *Staphylococcus aureus* and *Escherichia coli* at 62.5 mcg./ml. and 125 mcg./ml. respectively.

EXAMPLE 10

A. A mixture of 36 g. of N-(3,4-dimethoxyphenyl)-N-benzylamine and 15.3 g. of ethyl 6-bromocyclohexanone-2-carboxylate was maintained at about 35°C. for several days. Powdered zinc chloride (25 g.) was added and the mixture was heated at 125°C. for 1½ hours. The cooled mixture was slurried in water and extracted with ether. The ether extract was washed with 5% hydrochloric acid and water, dried and evaporated to dryness. The residual crude ethyl ester was treated with a solution of 24 g. of potassium hydroxide in 100 ml. of water and 100 ml. of ethyl alcohol at reflux temperature for 3 hours. The solution was evaporated to dryness under reduced pressure, the resulting residue was dissolved in water and the aqueous solution was extracted with 58% ether/n-hexane and acidified with 10% hydrochloric acid. The resulting solids were collected and recrystallized from tetrahydrofuran/n-pentane to give 7.1 g. of 9-benzyl-6,7-dimethoxy-1,2,3,4-tetrahydrocarbazole-4-carboxylic acid, m.p. 177°–179°C.

B. Following a procedure similar to that described in Example 1A but using 0.47 g. of sodium hydride in 110 ml. of benzene, 7.1 g. of 9-benzyl-6,7-dimethoxy-1,2,3,4-tetrahydrocarbazole-4-carboxylic acid, 1.46 ml. of thionyl chloride, 3.14 g. of N-phenylpiperazine, and 11 ml. of triethylamine (as acid-acceptor) in a small amount of benzene, there was obtained 2.8 g. of 4-[(4-phenyl-1-piperazinyl)carbonyl]-9-benzyl-6,7-dimethoxy-1,2,3,4-tetrahydrocarbazole, m.p. 133°–136°C. (ethyl acetate/ether/n-pentane).

C. Following a procedure similar to that described in Example 1B but using 2 g. of lithium aluminum hydride in 250 ml. of tetrahydrofuran and 26 g. of 4-[(4-phenyl-1-piperazinyl)-carbonyl]-9-benzyl-6,7-dimethoxy-1,2,3,4-tetrahydrocarbazole, there was obtained 10 g. of crude residue consisting largely of 4-[(4-pheny-1-piperazinyl)methyl]-9-benzyl-6,7-dimethoxy-1,2,3,4-tetrahydrocarbazole,-phenyl-yielded 4.9 g. of 4-[(4-phenyl-1-piperazinyl)methyl]-9-benzyl-6,7-dimethoxy-1,2,3,4-tetrahydrocarbazole dihydrochloride, m.p. 245°–247°C.

4-[(4-Phenyl-1-piperazinyl)methyl]-9-benzyl-6,7-dimethoxy-1,2,3,4-tetrahydrocarbazole dihydrochloride was found to be antibacterially effective against *Pseudomonas aeruginosa* at 125 mcg./ml.

EXAMPLE 11

A. Following a procedure similar to that described in Example 1A but using 0.72 g. of sodium hydride in 170 ml. of benzene, 10 g. of 9-benzyl-6-methoxy-1,2,3,4-tetrahydrocarbazole-4-carboxylic acid, 2.2 ml. of thionyl chloride, and 2.7 g. of ethylamine, there was obtained 6.5 g. of 4-ethylaminocarbonyl-9-benzyl-6-methoxy-1,2,3,4-tetrahydrocarbazole, m.p. 168°–169°C. (tetrahydrofuran/n-hexane).

B. Following a procedure similar to that described in Example 1B but using 1 g. of lithium aluminum hydride in one liter of tetrahydrofuran, and 3.6 g. of 4-ethylaminocarbonyl-9-benzyl-6-methoxy-1,2,3,4-tetrahydrocarbazole, and increasing the reflux time to 10 hours, there was obtained 4 g. of crude residue consisting largely of 4-ethylaminomethyl-9-benzyl-6-methoxy-1,2,3,4-tetrahydrocarbazole, which yielded 1 g. of 4-ethylaminomethyl-9-benzyl-6-methoxy-1,2,3,4-tetrahydrocarbazole hydrochloride, m.p. 233°–235°C.

EXAMPLE 12

A. Following a procedure similar to that described in Example 1A but using 0.72 g. of sodium hydride in 170 ml. of benzene, 10 g. of 9-benzyl-6-methoxy-1,2,3,4-tetrahydrocarbazole-4-carboxylic acid, 2.2 ml. of thionyl chloride, and 3.6 g. of propylamine, there was obtained 7 g. of 4-propylaminocarbonyl-9-benzyl-6-methoxy-1,2,3,4-tetrahydrocarbazole, m.p. 180°–181°C. (ethyl acetate).

B. Following a procedure similar to that described in Example 11A but substituting for the amide used therein an equivalent amount of 4-propylaminocarbonyl-9-benzyl-6-methoxy-1,2,3,4-tetrahydrocarbazole there is obtained 4-propylaminomethyl-9-benzyl-6-methoxy-1,2,3,4-tetrahydrocarbazole and the hydrochloride salt thereof.

By following a procedure similar to that described in Example 10A but substituting for N-(3,4-dimethoxyphenyl)-N-benzylamine an equivalent amount of the following amines:

N-(4-methylphenyl)-N-benzylamine;
N-(4-n-hexylphenyl)-N-benzylamine;
N-(4-tert-butylphenyl)-N-benzylamine;
N-(4-isopentyloxphenyl)-N-benzylamine; and
N-(4-methyl-3-methoxyphenyl)-N-benzylamine;
there are obtained respectively:

13. 9-benzyl-6-methyl-1,2,3,4-tetrahydrocarbazole-4-carboxylic acid;

14. 9-benzyl-6-n-hexyl-1,2,3,4-tetrahydrocarbazole-4-carboxylic acid;

15. 9-benzyl-6-tert-butyl-1,2,3,4-tetrahydrocarbazole-4-carboxylic acid;

16. 9-benzyl-6-isopentyloxy-1,2,3,4-tetrahydrocarbazole-4-carboxylic acid; and 17. 9-benzyl-6-methyl-7-methoxy-1,2,3,4-tetrahydrocarbazole-4-carboxylic acid.

The phenylbenzylamines used in the preparation of the carboxylic acids 13–17 above are obtained by reacting benzaldehyde with 4-methylaniline, 4-n-hexylaniline, 4-tert-butylaniline, 4-isopentyloxyaniline, and 4-methyl-3-methoxyaniline respectively, using the procedures described in U.S. Pat. No. 3,687,969.

By following a procedure similar to that described in Example 1A but substituting for 9-benzyl-6-methoxy-1,2,3,4-tetrahydrocarbazole-4-carboxylic acid an equivalent amount of the carboxylic acids 13-17 above, and for dimethylamine an equivalent amount of the following amines:

N-(n-hexyl)-N-methylamine;
dibenzylamine;
N-(benzyl)-N-methylamine;
di-n-hexylamine; and
diethylamine;

there are obtained respectively:

18. 4-(N-n-hexyl-N-methylaminocarbonyl)-9-benzyl-6-methyl-1,2,3,4-tetrahydrocarbazole;

19. 4-dibenzylaminocarbonyl-9-benzyl-6-n-hexyl-1,2,3,4-tetrahydrocarbazole;

20. 4-(N-benzyl-N-methylaminocarbonyl)-9-benzyl-6-tert-butyl-1,2,3,4-tetrahydrocarbazole;

21. 4-di-n-hexylaminocarbonyl-9-benzyl-6-isopentyloxy-1,2,3,4-tetrahydrocarbazole; and 22. 4-diethylaminocarbonyl-9-benzyl-6-methyl-7-methoxy-1,2,3,4-tetrahydrocarbazole.

By following a procedure similar to that described in Example 1B but substituting for 4-dimethylaminocarbonyl-9-benzyl-6-methoxy-1,2,3,4-tetrahydrocarbazole an equivalent amount of the amides 18–22 above there are obtained respectively:

23. 4-(N-n-hexyl-N-methylaminomethyl)-9-benzyl-6-methyl-1,2,3,4-tetrahydrocarbazole;

24. 4-dibenzylaminomethyl-9-benzyl-6-n-hexyl-1,2,3,4-tetrahydrocarbazole;

25. 4-(N-benzyl-N-methylaminomethyl)-9-benzyl-6-tert-butyl-1,2,3,4-tetrahydrocarbazole;

26. 4-di-n-hexylaminomethyl-9-benzyl-6-isopentyloxy-1,2,3,4-tetrahydrocarbazole; and 27. 4-diethylaminomethyl-9-benzyl-6-methyl-7-methoxy-1,2,3,4-tetrahydrocarbazole.

We claim:

1. 4-$R_1R_2NCH_2$-9-benzyl-6-$R_3$-7-$R_4$-1,2,3,4-tetrahydrocarbazole having the formula:

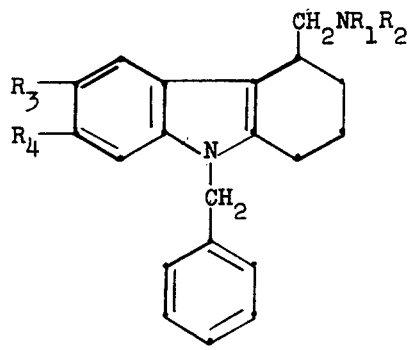

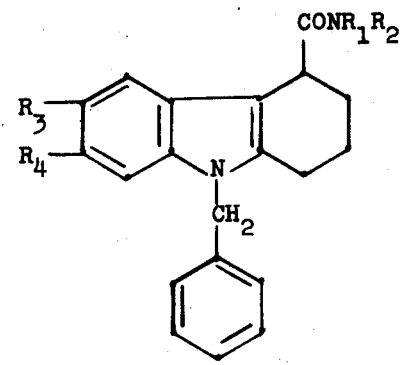

wherein
R₁ and R₂ are each hydrogen, lower-alkyl or benzyl, and
R₃ and R₄ are each hydrogen, lower-alkyl, or lower-alkoxy.

2. A compound according to claim 1 wherein $R_4$ is hydrogen.

3. 4-Dimethylaminomethyl-9-benzyl-6-methoxy-1,2,3,4-tetrahydrocarbazole according to claim 2.

4. 4-Benzylaminomethyl-9-benzyl-6-methoxy-1,2,3,4-tetrahydrocarbazole according to claim 2.

5. 4-R₁R₂NCO-9-benzyl-6-R₃-7-R₄-1,2,3,4-tetrahydrocarbazole having the formula:

wherein
R₁ and R₂ are each hydrogen, lower-alkyl, or benzyl, and
R₃ and R₄ are each hydrogen, lower-alkyl, or lower-alkoxy.

6. A compound according to claim 5 wherein $R_4$ is hydrogen.

7. 4-Dimethylaminocarbonyl-9-benzyl-6-methoxy-1,2,3,4-tetrahydrocarbazole according to claim 6.

8. 4-Benzylaminocarbonyl-9-benzyl-6-methoxy-1,2,3,4,-tetrahydrocarbazole according to claim 6.

* * * * *